United States Patent [19]

Eckhorn

[11] Patent Number: 5,413,103
[45] Date of Patent: May 9, 1995

[54] MICROPROBE AND PROBE APPARATUS
[75] Inventor: Reinhard Eckhorn, Kirchhain, Germany
[73] Assignee: Uwe Thomas Recording, Marburg, Germany
[21] Appl. No.: 176,221
[22] Filed: Jan. 3, 1994
[30] Foreign Application Priority Data
Jan. 19, 1993 [DE] Germany .................. 9300676 U
[51] Int. Cl.⁶ ............................................. A61B 5/04
[52] U.S. Cl. ..................................... 128/639; 128/731
[58] Field of Search ............... 128/630, 731, 639, 642, 128/634, DIG. 1, 733, 635; 604/27, 156, 164, 158; 606/171, 176; 607/116

[56] References Cited
U.S. PATENT DOCUMENTS
5,146,921 9/1992 Terwilliger et al. ............ 606/171 X
5,237,996 8/1993 Waldman et al. .................... 128/642

Primary Examiner—Lee S. Cohen
Assistant Examiner—Samuel Gilbert
Attorney, Agent, or Firm—Klaus J. Bach

[57] ABSTRACT

A microprobe for electrophysiological application, a microtube, fiber or wire probe is supported on a fixture within a tubular elastic support hose end has one end together with one end of the probe mounted on a clamping structure which is movably disposed on the fixture while the other end of the probe extends through a capillary guide tube from which its tip projects and the other end of the hose is mounted on the fixture and the hose maintained in a stretched state to engage the probe and provide radial support and a microdrive is connected to the clamping structure for axially moving the probe together with the one end of the hose and an apparatus including a plurality of independently movable probes.

16 Claims, 2 Drawing Sheets

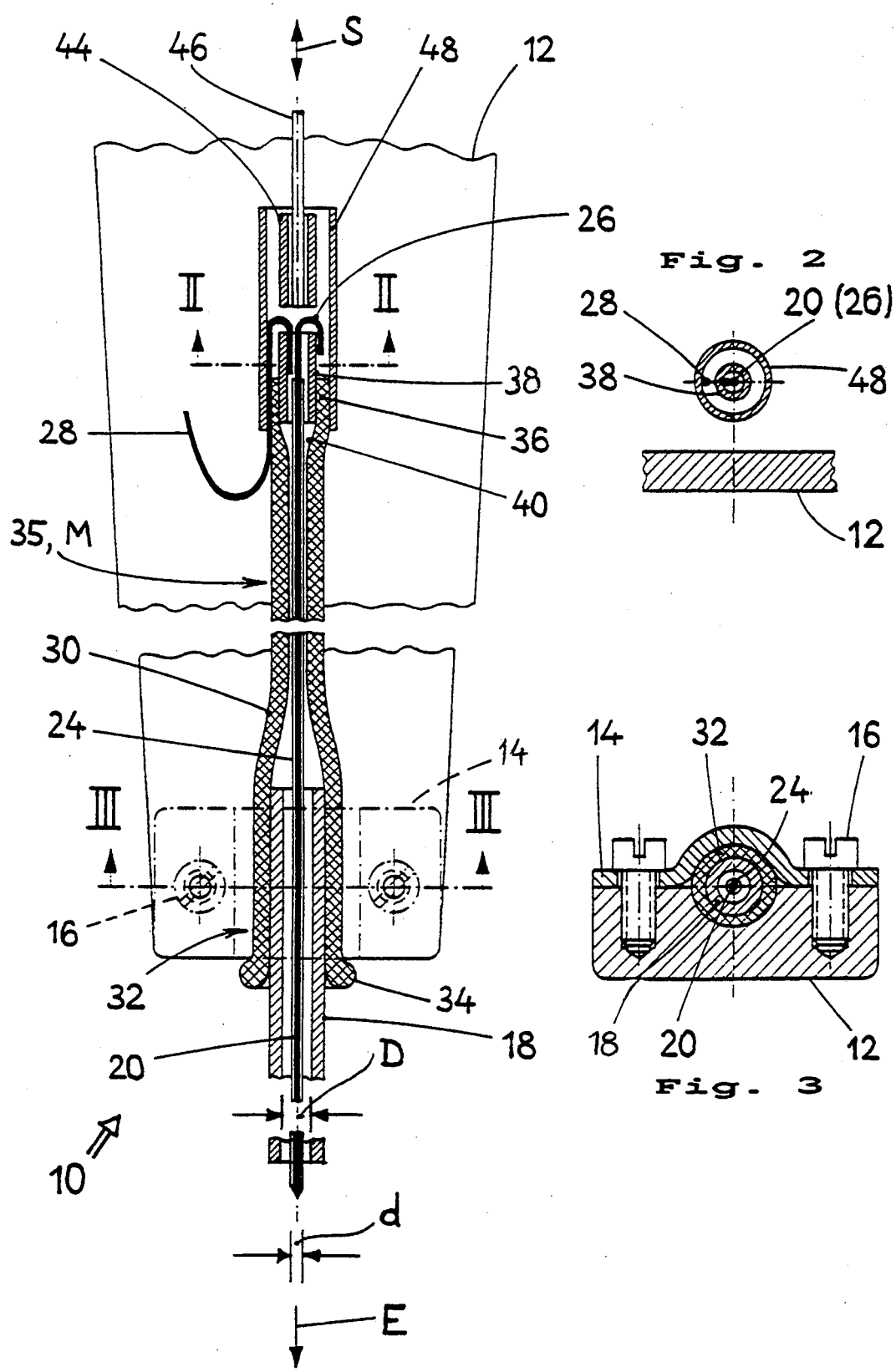

MICROPROBE AND PROBE APPARATUS

BACKGROUND OF THE INVENTION

The present invention relates to a microprobe for electrophysiological applications with micro-fiber sensors arranged in a guide channel so as to be axially movable therein in an accurately controllable manner and an apparatus including a plurality of such microprobes.

In medical and in biological research and in biophysics, fine probes in the form of electrodes or pipettes are needed for many applications, wherein a body or a particular structure must be sampled or inputs must be provided in a point-by-point fashion. If the probes have a relatively large diameter they are sufficiently stable to withstand the impression reaction forces, but they have a relatively large insertion cross-section so that they can cause undesirable and possibly painful injuries. Thin probes however easily kink and it is therefore necessary to guide and support them radially or example by a tube. This however requires a quite costly drive and coupling mechanism in order to advance the probe in steps which must be shorter than the so-called kinking length of the probe. The repetitive coupling procedures then cause undesirable vibrations of the probe and sliding of the probe in the coupling structure results in additive position errors.

There is accordingly a need for relatively long probes with thin shafts which are safely projected from kinking. In this connection "relatively long and thin" means dimensions wherein shaft length to shaft diameter are at a ratio of at least 10:1. Probes in this connection are microelectrodes, chemical and electrical sensors, tubular needles, pipettes, capillaries, etc., which are to be inserted into plastic-elastic structures, particularly into nerve and muscle tissues.

It is an important object of the present invention to provide improved probes and probe apparatus in an economical manner, wherein the probes, on one hand, are very thin and on the other, are so stable that they can be inserted into respective structures over distances, that is, to depths, which greatly exceed the probe kinking length. Novel and highly economical guide means are to be provided which safely prevent kinking.

SUMMARY OF THE INVENTION

A microprobe for electrophysiological application, a microtube, fiber or wire probe is supported on a fixture within a tubular elastic support hose and has one end together with one end of the probe mounted on a clamping structure which is movably disposed on the fixture while the other end of the probe extends through a capillary guide tube from which its tip projects and the other end of the hose is mounted on the fixture and the hose maintained in a stretched state to engage the probe and provide radial support and a microdrive is connected to the clamping structure for axially moving the probe together with the one end of the hose and an apparatus including a plurality of independently movable probes.

The preferred main support means according to the invention is an elongate elastic hose for each probe. It is engaged at its outer end by means of a clamp which preferably consists of stainless steel, extends across a guide lube and is mounted on a support fixture for the drive structure. The guide tube guides the probe in the desired insert direction. At the other, that is, its inner, end the probe and the hose which may consist, for example, of rubber, are connected by way of a clamp to a retaining pin or wire to a microdrive, by which the hose can be stretched to an exactly adjustable length. The probe tip can be accurately positioned in small advancing steps by the microdrive, that is, accurately controlled translational movement can be achieved.

The elastic hose keeps the probe kink-free since the radially acting kinking forces are smaller, by far, than the counteracting forces of the stretched hose, whereby the kinking length of the probe can be increased typically by 10 to 100 times. Upon stretching, the hose closely surrounds the probe and firmly engages it all around over most of its length, at least over the length thereof in which movement forces are applied thereto. Even microwaves unwound from a coil can be used for moving the probe in this manner without kinking since they are only subjected to tensional forces. Suitable hoses are generally available highly elastic silicon rubber hoses as they are used, among others, for hose pumps.

With such a secure hose support, relatively large axial forces can be applied to the tip of the probe which is very helpful when relatively tough structures have to be pierced. The tip insertion forces are about of the same size as the elastic axial forces applied to the rubber hose. Also, with probes which are difficult or expensive to manufacture, the penetrating force applicable to a tissue can be determined by appropriate selection of hose length and the extent to which the hoses are stretched so that neither the probe tip nor the probe shaft is damaged by the resistance of the respective tissue.

The inner diameter of the guide tube which may be a capillary tube is preferably about 20% larger than the probe diameter because contamination such as dust could inhibit sliding movement or even lock the probe in the guide tube; guide tubes with too large a diameter would permit undesirable side movement of the probe, for example, when the tissue provides no side support. In order to facilitate sliding movement and prevent mechanical locking of the probe in the guide tube (for example, by crystallized liquid or blood clots), the gap between the probe and the guide tube is preferably filled with a sterile lubricant such as silicon oil. This, furthermore, attenuates probe vibrations within the capillary guide tube and, as a result, reduces "microphone" potentials in connection with high-impedance probes.

BRIEF DESCRIPTION OF THE DRAWINGS

FIG. 1 is an axial cross-sectional view of a microprobe with its support;

FIG. 2 is a cross-sectional view along line II—II of FIG. 1;

FIG. 3 is a cross-sectional view along line III—III of FIG. 1; and

DESCRIPTION OF THE PREFERRED EMBODIMENT

Figure 4:
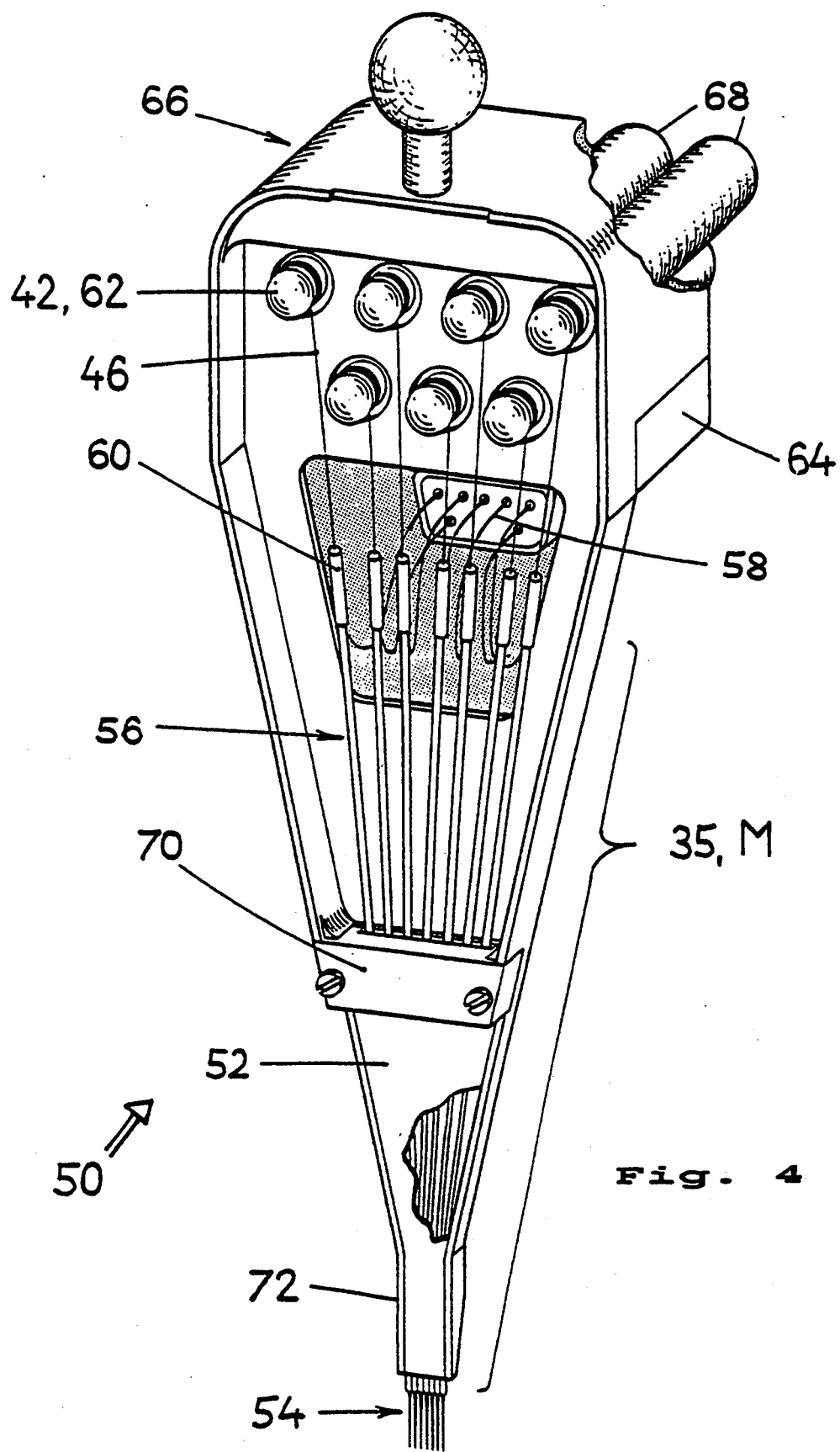
FIG. 4 is a perspective view of a probe apparatus with support and drive.

FIG. 1 shows the microprobe which is designated generally by the reference numeral 10. It includes a support or fixture 12 on which a clamp 14 is mounted by screws 16 and which engages a capillary-like guide tube 18 of steel with the end 32 of a support hose 30 disposed between the clamp and the guide tube 18. The hose 30 forms a support structure for the probe 20, whose outer end 22 projects beyond the outer end 32 of the hose and is provided with a pointed tip. The inner diameter D of the capillary tube 18 of steel is about 1.2 times the outer diameter d of the probe 20 which has a slidable insulative coating 24.

Over the length M which includes most of the length of the probe 20, it is disposed within the passage 40 through the hose 30 by which it is firmly engaged and which forms a clamping structure 35 for the probe. Such engagement is achieved by firmly engaging the inner end 36 of the hose 30 between an inner mounting tube 38 and an outer clamping tube 48. The outer clamping tube 48 also engages a connector lead 28 which is in electrical contact with the inner end 26 of the probe 20 by means of a crimp structure. FIG. 2 shows this arrangement in cross-section.

An inner bushing 44 which is firmly mounted to the clamping tube 48 is connected to a pin or wire 46 which leads to a microdrive 42 (not shown in detail). The microdrive tensions the hose 30 whose clamping section 35 then stretches and firmly engages the probe 20 over its length M all around in a force-transmitting fashion. In this manner the probe 20 can be moved forward by releasing the drive wire and backward by further tensioning of the support hose for movement of the probe through the capillary guide tube 18 relative to the fixture 12—see the cross-sectional view of FIG. 3. The outer end 32 of the hose is provided with a bulge 34 which facilitates its retaining by the clamp 14.

The probe apparatus 50 is shown in FIG. 4 with a plurality of microprobes 10. It includes a carrier 52 which supports a group of probes 54 in a parallel guide structure 72. Again, each probe 20 is enclosed by a support hose 30 such that group 56 of support hoses is formed wherein the support hoses are individually held by clamping structures 60 which, at the same time, engage the respective connector leads 58 to the group of probes 54. Insulated wires or strings 46 are connected to the clamping structures 60 and are connected to control heads 62 which may be spools mounted on the shafts of motor drives 68 supported in motor supports 64 combined in a drive unit 66. Adjacent thereto are the probe connector leads 58. The hose group 56 is engaged at its lower end by a mounting bridge 70 wherein each hose 30 is mounted and clamped to its guide tube 18.

In the embodiment shown in FIG. 4 the apparatus 50 includes seven microprobes 54. The micro control heads 62 of the drive units 66 are electronically controlled and independently operable by DC drive motors 68 (with a typical transmission ratio of 1:4000). A steel cable of, for example, 200 $\mu$m diameter which is coated with polyfluorofetraethylene (Teflon) is wound on a drum of, for example, 3.5 mm diameter which is disposed on the output shaft of a transmission drive. The drive motors 68 each are provided with position sensors (not shown) which provide signals that can be stored in a computer, for example, 10 pulses per rotation of the drum which corresponds to a circumferential resolution of 0.1 $\mu$m.

Such a probe operating system has been used, among others, for the insertion of microelectrodes through the closed dura into the brain of permanently prepared cats and monkeys. In one embodiment a seven-channel system was employed with commercially available insulated wire probes with an outer diameter of 50 to 100 $\mu$m and quartz fiber probes with tips having points cut in two different ways; either tips with metal cores or extra cellular sensing of electrical neural signals or pipettes For the injection or for the electrophoretic introduction of compounds and for the sensing of electrical signals.

Recordings in the visual outer brain area were taken with a probe apparatus 50 having a group 54 of electrodes 20, which were inserted through the dura of cats and monkeys up to a depth of 20 mm. With several fiber microelectrodes 20 of, for example, 3 to 7 Ohm impedance at 1 kHz, activity potentials of single cells were recorded in a stable manner over extended periods while another probe 20 was moved forward at a speed of 1 to 10 $\mu$m/sec, that is, extremely slowly, to a position with isolated single cell activity.

Only little mechanical influence of the sensing position of other electrodes 20 by a moving probe is obtained as a result of easy sliding properties of the probe in the rubber hose support structure 30, the small diameter of the probes 20 and their friction-reducing coating. Consequently, interference signals are generally negligible so that the same high-impedance electrodes can measure also local slow brain activity potentials (0-150 Hz) and multiple activities during continuous electrode movement.

At the point of penetration the geometric arrangement of the electrodes 20 depends on the distance of the guide capillaries 18 from one another. With an outer diameter of, for example, 250 $\mu$m (inner diameter D=100 $\mu$m) a suitable distance is 500 $\mu$m. Also other, particularly smaller, distances can be achieved, for example, distances down to 200 $\mu$m, with fiber probes 20 of, for example, 70 $\mu$m probe diameter (d). Also concentric, linear or other electrode arrangements could be realized with relatively simple, known means, for example, suitable arrangement of the steel capillaries 18 or exchangeable guide structures 72 (70). With an appropriately prepared probe arrangement, the probe tips 22 can be accurately inserted into the desired areas. This is particularly advantageous if signals from two or three different brain areas have to be recorded concurrently and the probe tips 22 have to be driven for this purpose to special positions in order to analyze in the recording area the dynamic cooperation of activated nerve groups.

The precise mechanical drive makes a reliable probe position control by means of the rubber hose thrust movement possible. Malfunctions because of the probes getting stuck in the relatively short capillary guide tubes of steel are rare as the relatively large advancing forces of the elastic hoses 30 easily overcome the friction in the tubes. The clamping structure 35 begins immediately adjacent the inner end of the probe 26, and in this area of the hose 30, the probe 20 is firmly engaged by the hose all around so as to provide for good force transmission between the probe and the hose and also preventing kinking of the probe. Because of the continuous probe engagement (35, M), even repeated movement steps or changes in the direction of movement do not cause any added position errors since the mounting arrangement, in principle, cannot generate any error addition; if anything, only the microdrive 42 itself could cause an addition of errors, As a result, the controlled probe tip 22 will arrive at a particular desired position no matter whether the advance is performed in a single translation step or in several partial steps.

The rubber hose engagement permits the use of all kinds of slim probes 20 down to a probe shaft diameter of about d$\approx$25 $\mu$m. With even smaller probes, handling may become difficult. It is possible to use electrodes for the electrical stimulation and for the sensing of neural and muscle signals as well as recording, and injection pipettes and acupuncture needles. (Larger diameter probes, for example, with 200 μm outer diameter and above can also be used but they are usually strong enough so that they can be operated by known drive arrangements.) Depending on the shaft diameter d of the probes 20 it is advisable to exchange the capillary guide tubes of steel which can be done rapidly.

When compared with prior art drive arrangements for fiber microelectrodes, the arrangement according to the invention has additional advantages. The guide system (30, 20) is much smaller and lighter and it is easier and less expensive to manufacture than the prior art manipulators. It also can be used in connection with very fine probes 20 so that little space is displaced in the tissue being penetrated and little damage is caused. No cumulative position errors occur either. Smooth accurate movement of the probes with relatively large penetration depths can be achieved. The arrangement causes hardly any error signals of mechanical origin and also is not subject to such errors. Furthermore, the arrangement can use any of a large number of commercially available microdrives. A good number of such small probes 20 can be provided in a compact group 54 and they can be independently controlled in spite of their small distance from one another.

The present invention is not limited to the arrangements described in detail; it can, particularly, also be utilized for macro technical applications. It is noted however, that, for a preferred embodiment of a microprobe 10 for electro physiological applications, at least one microtube, fiber or wire-like probe 20 is slidably disposed within a guide hose 30 so as to be movable relative to the fixture 12 supporting the arrangement. The hose 30 surrounds the major portion M of the probe 20 in a clamping structure 35 which is movable by means of a microdrive 42. The clamped hose end 32 is provided with a bulge 34 so that the hose end can be safely retained by the clamp 14. The inner end 26 of the probe is in contact with a connector lead 28, within a mounting tube 38, which extends from the mounting tube 38 and is surrounded by an outer clamping tube 48 engaging the inner end 36 of the hose and also the connector lead 28. The outer clamping tube 48 is connected lo the microdrive 42. The hose 30 comprises silicone rubber. The probe 20 is provided with a slidable insulative coating at least on its main portion M. A probe apparatus includes supported on a carrier 52 a group of probes 54 which is movable via a group of hoses 56 by means of control heads 62. The hoses 30 arranged in the group 56 in close side-by-side relationship ere engaged by 8 mounting bridge 70 where the guide tubes are mounted to the hoses and from where the guide tubes extend through 8 parallel-guide structure 72 and project slightly therefrom with the probes extending from the guide tubes and being independently movable by stretching of the respective hoses or releasing them by movement of the respective clamping tubes 48.

All features covered by the claims and presented in the description and the drawings, with the advantages described, and with the various design features and spatial arrangements are considered to be inventive either alone or in the various combinations.

What is claimed is:

1. A microprobe for electrophysiological applications, comprising a base fixture, a probe selected from the group consisting of one of a microtube, a fiber and a wire supported on said fixture within a tubular support body which closely surrounds said probe so as to provide radial support for said probe, said probe and said support body having one of their ends mounted together in a clamping structure which is movably disposed on said fixture, a capillary guide tube mounted on said fixture, another end of said probe extending through said capillary guide tube mounted on said fixture and having an inner end received in said tubular support body and an outer end projecting from said fixture for guiding and slidably supporting said probe, said probe having a tip projecting rum said capillary guide tube, and a microdrive mounted on said base fixture and operatively connected to said clamping structure for axially moving said clamping structure together with said one end of said tubular support body and said probe on said base fixture.

2. A microprobe according to claim 1, wherein said tubular support body closely engages said probe over most of its length.

3. A microprobe according to claim 1, wherein said support body is an elastic hose which has one end engaged by said clamping structure and which is mounted at another end firmly onto said base fixture, said microdrive with said clamping structure being adapted to maintain said elastic hose in a stretched state in which it is contracted for engagement with the probe extending therethrough.

4. A microprobe according to claim 3, wherein the other end of said support hose is mounted to said base fixture by a clamp engaging said hose and said capillary guide tube within said hose.

5. A microprobe according to claim 4, wherein said hose extends beyond said clamp and, adjacent said clamp, includes a bulge for firmly retaining said hose in said clamp under axial stress.

6. A microprobe according to claim 4, wherein said capillary guide tube is a steel tube with an inner and outer diameter, said inner diameter being not more than 1.2 times an outer diameter of said probe.

7. A microprobe according to claim 6, wherein said capillary guide tube has a length of at least ten times the outer diameter said probe.

8. A microprobe according to claim 3, wherein said probe is provided with an insulative low-friction coating at least where it is engaged by said hose so as to permit relative movement between said probe and said hose.

9. A microprobe according to claim 3, wherein said hose consists of silicone rubber.

10. A microprobe according to claim 1, wherein said one end of said probe is in contact with a connector lead within said clamping structure, said connector lead extending from said clamping structure so as to permit relative movement of said clamping structure on said fixture.

11. A microprobe according to claim 10, wherein said clamping structure comprises a mounting tube ,on which the one end of said tubular support body is disposed and a clamping tube extending around the one end of said hose so as to firmly engage it between the mounting tube and the clamping tube.

12. A microprobe according to claim 11, wherein said clamping tube is operatively connected to said microdrive by an operating wire capable of pulling said clamping structure so as to axially stretch said elastic hose and, at the same time, retract said probe, or release said wire so as to permit axial contraction of said hose for axial advancement of said probe while providing firm radial support for said probe.

13. A microprobe apparatus comprising a fixture with a plurality of probes mounted thereon, said probes being supported on said fixture within elastic guide hoses arranged adjacent one another, each of said hoses closely surrounding one of said probes so as to provide radial support for said probe, each probe and guide hose having one of their ends mounted together in a clamping structure with another end of each guide hose being firmly mounted to said base fixture, a capillary guide tube mounted on said base fixture for each probe and having an inner end received in said other end of said elastic guide hose and extending therefrom to a front end of said fixture, said probes each having a tip projecting from its capillary guide tube, and a microdrive with a control head for each of said clamping structures and adapted to hold said elastic hose in a stretched state in which said hose is constricted and firmly engages said probe so as to provide axial support thereto, said microdrive being adapted to axially move said clamping structure backward to retract said probe while said elastic hose is further stretched and firmly engages and supports said probe or to advance said probe by moving said clamp structure forward whereby said elastic hose contracts axially while still providing firm radial support to said probe.

14. A microprobe apparatus according to claim 13, wherein the other end of each said guide hoses are disposed closely adjacent one another and are all engaged by a single clamping bridge.

15. A microprobe apparatus according to claim 13, wherein, at its front end, said fixture includes a parallel guide structure for said capillary guide tubes.

16. A microprobe apparatus according to claim 13, wherein said control heads are operable by said microdrives including transmissions which are all together mounted in a drive unit mounted on said base fixture. b1 a capillary guide tube mounted on said fixture

* * * * *